United States Patent [19]

Tsukada et al.

[11] Patent Number: 5,229,366
[45] Date of Patent: Jul. 20, 1993

[54] PEPTIDE-CONTAINING POLYETHYLENE GLYCOL DERIVATIVES AND APPLICATION THEREOF

[75] Inventors: Yoshihisa Tsukada; Atsushi Orikasa, both of Minami-ashigara, Japan

[73] Assignee: Fuji Photo Film Co., Ltd., Kanagawa, Japan

[21] Appl. No.: 780,081

[22] Filed: Oct. 21, 1991

[30] Foreign Application Priority Data

Oct. 23, 1990 [JP] Japan .................................. 2-285172
Nov. 21, 1990 [JP] Japan .................................. 2-316441
Nov. 30, 1990 [JP] Japan .................................. 2-333717

[51] Int. Cl.$^5$ ...................... A61K 37/02; C07K 17/08
[52] U.S. Cl. ........................ 514/12; 514/18; 514/19; 530/331
[58] Field of Search ................. 514/18, 19, 12; 530/331

[56] References Cited

FOREIGN PATENT DOCUMENTS 280610 8/1988 European Pat. Off. .
91/12263 8/1981 PCT Int'l Appl. .
87/00056 1/1987 PCT Int'l Appl. .

OTHER PUBLICATIONS

Pierschbacher, Michael D. & Ruoslahti, Erkki, "Cell Attachment Activity of Firbronectin Can Be Duplicated By Small Synthetic Fragments of the Molecule", May, 1984, Nature vol. 309.
Humphries, et al., *J. Biol. Chem.*, 262: 6886–6892 (1987).
Saiki et al., *Int. J. Biol. Macromol.*, 11:23–25 (1989).

*Primary Examiner*—Ronald W. Griffin
*Attorney, Agent, or Firm*—Sughrue, Mion, Zinn, Macpeak & Seas

[57] ABSTRACT

A peptide-containing polyethylene glycol derivative represented by the following general formula [I] or [II]:

[Structure I: $CH_3-(OCH_2CH_2)_n-O-$ triazine ring with two $R^1$ substituents]

[Structure II: two $CH_3-(OCH_2CH_2)_n-O-$ groups attached to triazine ring with one $R^1$ substituent]

wherein each $R^1$ independently represents a peptide residue represented by the following general formula [IIIa] or [IIIa]:

-([X]-Arg-Gly-Asp-[Y])$_m$-Z    [IIIa]

([X]-Glu-Ile-Leu-Asp-val-Pro-Ser-Thr-[Y])$_m$    (IIIb)

wherein Arg, Gly, Asp, Glu, Ile, Leu, val, Pro, Ser and Thr represent arginine, glycine, aspartic acid, glutamic acid, isoleucine, leucine, valine, proline, serine and threonine residue respectively; [X] and [Y] each represents an amino acid or peptide residue which may be present or absent; n is an integer ranging from 1 to 150; m is an integer ranging from 1 to 5 and Z represents —OH or —NH$_2$, provided that the peptide residue [IIIb] and the triazine ring is bonded at the position of [X] (if [X] is absent, at the position of Glu) or [Y] (or if [Y] is absent, at the position of Thr) or a salt thereof. The compound is useful as an effective ingredient of a composition for inhibiting adhesion of animal cells comprising or for inhibiting coagulation/cohesion of blood platelets.

13 Claims, No Drawings

PEPTIDE-CONTAINING POLYETHYLENE GLYCOL DERIVATIVES AND APPLICATION THEREOF

BACKGROUND OF THE INVENTION

1. Field of the Invention

The present invention relates to a polyethylene glycol derivative comprising an arginine-glycine-aspartic acid tripeptide unit or glutamic acid-isoleucine-leucine-aspartic acid-valine-proline-serine-threonine (SEQ ID 00:1) octapeptide unit or salts thereof as well as a composition for inhibiting adhesion of animal cells and a composition for inhibiting c oagulation/cohesion of blood platelets.

2. Prior Art

Fibroncetin is a protein involved in the cell-extracellular substrate cohosion and is likewise thought to be involved in coagulation of blood platelets and the metastasis of cancer. These interactions are mediated by a series of receptors present in the cell surface region, it is confirmed that these receptors can specifically recognize an amino acid sequence: arginine-glycine-aspartic acid (hereinafter referred to as "Arg-Gly-Asp") of the fibronectin although the fibronectin is a macromolecule having a molecular weight of about 250,000 and there has been reported that the sequence plays an important role in the interaction between the receptors and the fibronectin (Nature, 309, 1984, p. 30). Since then, there have been conducted many studies in which an oligopeptide or polypetide having such an amino acid sequence: Arg-Gly-Asp is used.

There have been reported various studies, such as a method for inhibiting the coagulation of blood platelets by the use of various linear and cyclic oligopeptides having an Arg-Gly-Asp sequence (Polymer Preprints, Japan, 38, 1989, p. 3149; Japanese Unexamined Patent Publication (hereinafter referred to as "J. P. KOKAI") No. Hei 2-174797); a method in which a peptide having an Arg-Gly-Asp sequence is used as a cell movement-inhibiting agent (J.P. KOKAI No. Hei 2-4716); and a method using, as a cell-adhesive membrane, a PMMA film on which Arg-Gly-Asp sequences are immobilized (Polymer Preprints, Japan, 37, 1988, p. 705). In addition, J.P. KOKAI Nos. Hei 1-309682 and Hei 1-305960 disclose a method which comprises covalently bonding peptides having Arg-Gly-Asp sequences as essential structural units to a polymer and in which the resulting product is used as a substrate for cultivating animal cells or for biological composite artificial organs and J.P. KOKAI No. Sho 64-6217 discloses a method in which a polypeptide having Arg-Gly-Asp-Ser sequences is used as a platelet protective agent for blood taken out of the body. Further, there has been known a method comprising inhibiting the metastasis of cancer by the use of an oligopeptide having Arg-Gly-Asp sequences or a polypeptide having the sequence as repeating units (Int. J. Biol. Macromol., 11, 1989, p. 23; ibid, 11, 1989, p. 226; and Jpn. J. Cancer Res., 60, 1989, p. 722).

Moreover, it has recently been proved that cell-adhesive sequences other than the Arg-Gly-Asp are also present in the fibronectin molecule and one of these has become of major interest recently, which is a CSI peptide (comprising a glutamic acid-isoleucine-leucine-aspartic acid-valine-proline-serine-threonine sequence) (SEQ ID No: 1) present in the IIICS (type III homology connecting segment) region (J. Biol. Chem., 262, 1987, p. 6886). This peptide is recognized by the fibronectin receptor like the Arg-Gly-Asp peptide and has been thought to be involved in the adhesion specificity of the fibronectin. It has presently been proved that the minimum unit capable of exhibiting such adhesion activity is an octapeptide having a glutamic acid-isoleucine-leucine-aspartic acid-valine-proline-serine-threonine sequence (hereinafter abbreviated to as "EILDVPST") (SEQ ID No: 1) (J. Cell Biol., 107, 1988, p. 2189).

On the other hand, polyethylene glycol is an amphiphathic synthetic polymer having both hydrophilic and hydrophobic properties. There has been proposed a method for modifying the properties of enzymes by the use of polyethylene glycol (Trends in Biotech., 4, 1986, p. 68) and there has been succeeded in the modification of properties of various enzymes through the introduction of the enzymes into the polyethylene glycol derivatives. However, there has not yet been known a compound obtained by introducing an oligopeptide having an Arg-Gly-Asp sequence or a polypeptide having the sequences as repeating units into the polyethylene glycol derivative. It would be anticipated that the resulting compound has an improved ability of binding to receptors and an improved stability in the blood.

SUMMARY OF THE INVENTION

Accordingly, an object of the present invention is to provide a polyethylene glycol derivative comprising an arginine-glycine-aspartic acid tripeptide unit or glutamic acid-isoleucine-leucine-aspartic acid-valine-proline-serine-threonine (SEQ ID No: 1) octapeptide unit or salts thereof and a method for preparing the same.

Another object of the present invention is to provide a composition for inhibiting adhesion of animal cells and a composition for inhibiting coagulation cohesion of blood platelets.

According to an aspect of the present invention, there is provided a peptide-containing polyethylene glycol derivative represented by the following general formula [I] or [II];

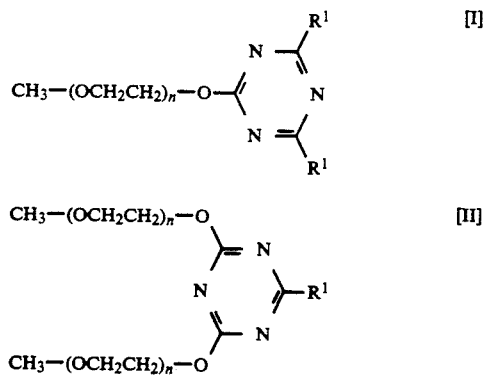

wherein $R^1$ independently represents a peptide residue represented by the following general formula [IIIa] or [IIIb];

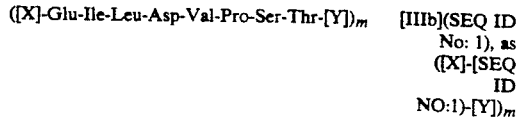

wherein Arg, Gly, Asp, Glu, Ile, Leu, Val, Pro, Ser and Thr represent arginine, glycine, aspartic acid, glutamic acid, isoleucine, leucine, valine, proline, serine and threonine residues respectively; [X] and [Y] each represents an amino acid or a peptide residue which may be present or absent; n is an integer ranging from 1 to 150; m is an integer ranging from 1 to 5; and Z represents —OH or —NH₂, or a pharmaceutically acceptable salt thereof.

According to another aspect of the invention, there is provided a composition for inhibiting adhesion of animal cells comprising, as an effective ingredient, the peptide-containing polyethylene glycol derivative defined above or a salt thereof.

According to further aspect of the invention, there is provided a composition for inhibiting coagulation/cohesion of blood platelets comprising, as an effective ingredient, the peptide-containing polyethylene glycol derivative defined above or a salt thereof.

DETAILED DESCRIPTION OF THE PREFERRED EMBODIMENTS

The present invention will hereinafter be explained in more detail.

The peptide-containing polyethylene glycol derivatives of the present invention are represented by the following general formula [I] or [II];

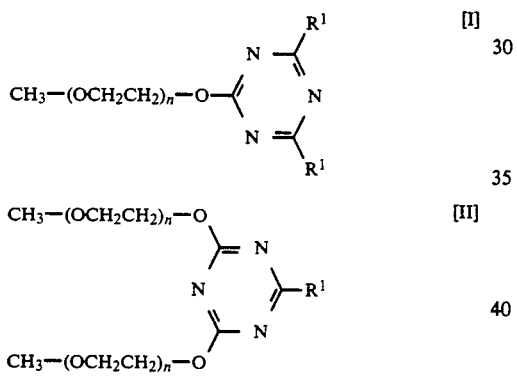

In the formulae [I] and [II], ionic groups present in the molecule may form salts with appropriate counter ions, and each R¹ independently represents a peptide residue represented by the following general formula [IIIa] or [IIIb];

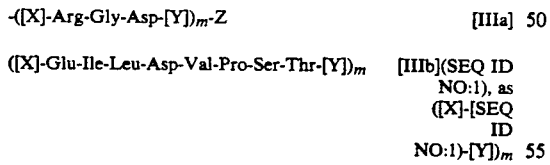

In the formulae [IIIa] and [IIIb], Arg, Gly, Asp, Glu, Ile, Leu, Val, Pro, Ser and Thr represent arginine, glycine, aspartic acid, glutamic acid, isoleucine, leucine, valine, proline, serine and threonine residues respectively. [X] and [Y] independently represents an amino acid or peptide residue which may be independently present or absent. If one or both of them are present, they preferably represent an amino acid residue selected from the group consisting of serine, glycine, valine, asparagine, proline, cysteine and threonine residues or a peptide residue constituted by the foregoing amino acid residues, and the number of amino aci residues constituting the peptide residue is preferably 2 or 3. In particular, [X] preferably represents a glycine residue and [Y] preferably represents a serine residue or a serine-proline peptide residue or preferably both [X] and [Y] are absent. The number of n is an integer ranging from 1 to 150, preferably 5 to 120, m is an integer ranging from 1 to 5, preferably 1 to 3, and Z represents —OH or —NH₂.

The peptide residue [IIIb] is bonded to the triazine ring at the position [X] (or if [X] is absent, at the position of Glu residue) or [Y] (or if [Y] is absent, at the position of Thr residue).

As the salts of the compounds of the present invention, there may preferably be mentioned, for instance, sodium, potassium, ammonium and magnesium salts as well as hydrochlorides, sulfates, nitrates and acetates.

The number average molecular weight of the compound according to the present invention preferably ranges from 5,000 to 15,000.

Preferred examples of the compounds according to the present invention will be listed below, but the present invention is by no means limited to these specific examples. In this respect, the following abbreviations are used for expressing amino acid residues in the description given below.

Arginine: Arg (or R)
Glycine: Gly (or G)
Aspartic acid: Asp (or D)
Glutamic acid: Glu (or E)
Isoleucine: Ile (or I)
Leucine: Leu (or L)
valine: Val (or V)
Proline: Pro (or P)
Serine: Ser (or S)
Threonine: Thr (or T)

Examples of the Compounds:

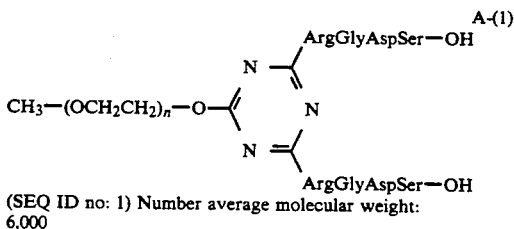

(SEQ ID no: 1) Number average molecular weight: 6,000

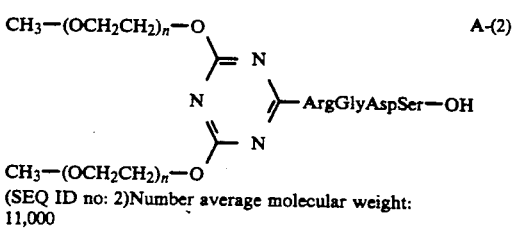

(SEQ ID no: 2) Number average molecular weight: 11,000

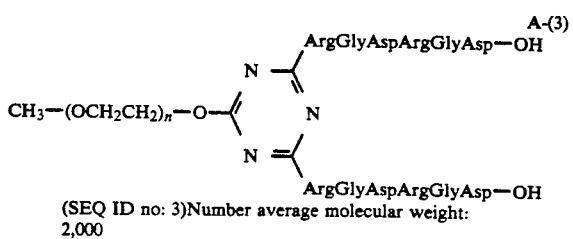

(SEQ ID no: 3) Number average molecular weight: 2,000

-continued

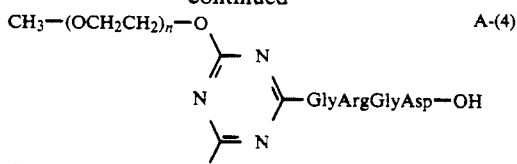
A-(4)
(SEQ ID no: 4) Number average molecular weight: 1,500

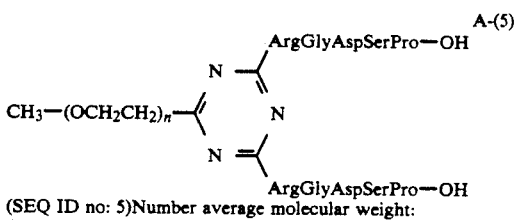
A-(5)
(SEQ ID no: 5) Number average molecular weight: 6,000

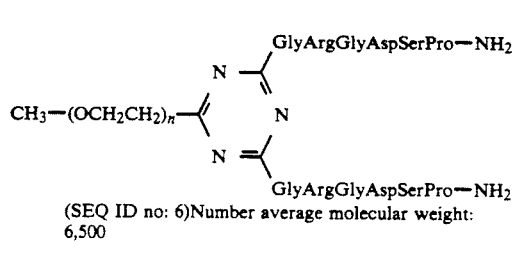
A-(6)
(SEQ ID no: 6) Number average molecular weight: 6,500

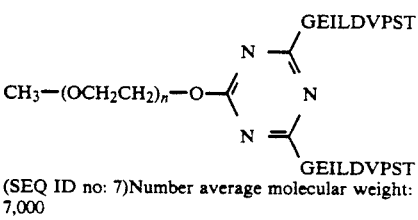
B-(1)
(SEQ ID no: 7) Number average molecular weight: 7,000

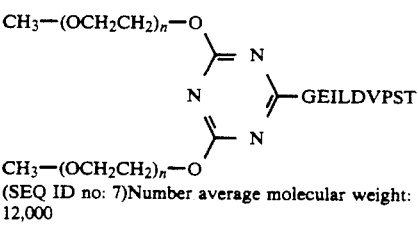
B-(2)
(SEQ ID no: 7) Number average molecular weight: 12,000

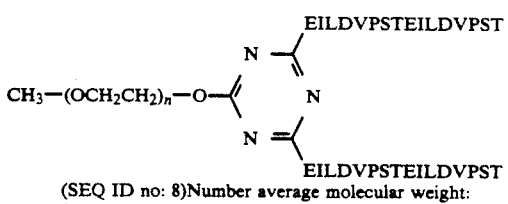
B-(3)
(SEQ ID no: 8) Number average molecular weight: 9,000

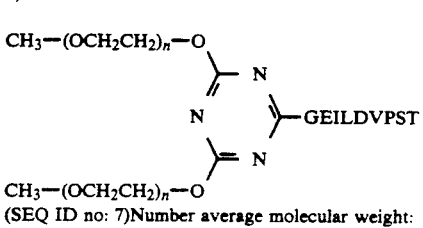
B-(4)
(SEQ ID no: 7) Number average molecular weight: 3,500

It is expected that the compounds of the present invention exhibit an improved ability of binding to receptors and high stability in the blood and the compounds can be used for inhibiting the adhesion of animal cell and the coagulation of platelets and activating the lymphocyte while making the most use of the fact that a site of the peptide, RGD or ELDVPST (SEQ ID NO:1), has an ability of binding to the fibronectin receptors present in the surface region of, for instance, cancer cells, platelets, lymphocytes.

The method for preparing the compounds will now be described in detail below. The compounds according to the invention may be prepard by, for instance, a method comprising the following 4 steps:

① Synthesis of polyethylene glycol derivatives of the formula IV] or [V]:

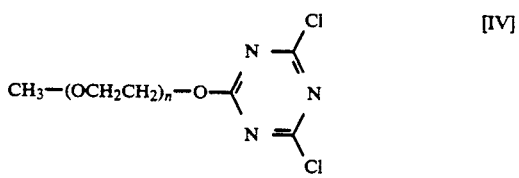
[IV]

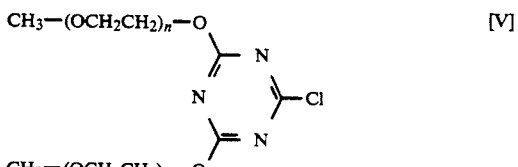
[V]

② Preparation of protected peptides by sequential extension of peptide length with protected amino acids ③ Synthesis of the compounds of formula [VI] or [VII] by introduction of protected peptides into the polyethylene glycol derivatives:

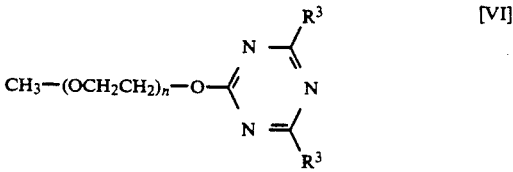
[VI]

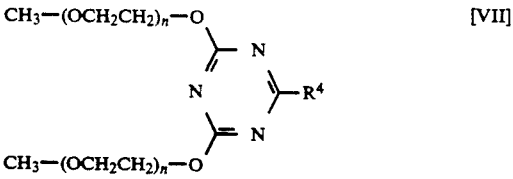
[VII]

wherein $R^3$ and $R^4$ each represents a protected peptide residue represented by the formula [IIIa] or [IIIb].

④ Removal of protective groups and purification
Each step will be detailed below.

① The compounds represented by the general formula [IV] and [V] can be synthesized by, for instance, the methods disclosed in Biochem. Biophys. Res. Commun., 83, 1978, p. 385 and Life Sciences, 33, 1983, p. 1467 and the compound the formula [V] is also commercially available.

② As the method for sequential extension of the peptide length with protected amino acids, effectively used are, for instance, currently known methods such as those detailed in "Fundamentals and Experiments of Peptide Synthesis", written by IZUMIYA et al., published by Maruzen Publishing Company and "PRINCIPLES OF PEPTIDE SYNTHESIS", "THE PRACTICE OF PEPTIDE SYNTHESIS", written by Bodanszky, Springer Verlag, N.Y. In the condensation reaction, either of the DCC-additive method, the azide method, the anhydrous mixed acid method and the activated ester method may be employed, but the best result can be obtained by the DCC-additive method in which 1-hydroxybenzotriazole and dicyclohexylcarbodiimide are used in combination.

③ The compounds of the formula [VI] and [VII] may be prepared by reacting polyethylene glycol derivatives represented by the formula [Iv] and [v] with protected peptides at room temperature in a solvent in which they are soluble, in the presence of a base with stirring.

④ The conditions for the removal of the protective groups greatly vary depending on the kinds of the protective groups used. The removal of the protective groups is in general performed by catalytic hydrogenation or by the use of trifluoroacetic acid, anhydrous hydrogen fluoride, a trifluoromethanesulfonic acid-thioanisole mixed system or a trifluoroacetic acid-thioanisole mixed system, but various other means may also be employed depending on the kinds of the protective groups. In addition, the purification of the final product can be performed by the gel filtration technique.

In the present invention, the number average molecular weight can be evaluated on the basis of the result determined by gel permeation chromatography (GPC). The conditions for the GPC measurement are as follows:

G1000H$_8$

Excrusion limit of molecular weight: 1000

Column size: 7.51 D×600 mm (1 column)

G2000H$_8$

Excrusion limit of molecular weight: 10000

Column size: 7.51 D×600 mm (2 columns)

G2500H$_8$

Excrusion limit of molecular weight: 20000

Column size: 7.51 D×600 mm (1 column)

Solvent: tetrahydrofuran

Flow rate: 1 ml/min

Column temperature: 40° C.

Detector: combination of UV and IR

Calibration curve is prepared by using TSK Standard Polyethylene Oxide as a reference substance.

The number average molecular weight is determined by the usual method as disclosed in "Experimental Methods in Polymer Science", edited by Society of Polymer Science Jap., 1981, Tokyo Kagaku Dojin Publishing Company, pp. 204–208, i.e., the segment method. That is, the number average molecular weight is determined by dividing the resulting chromatogram into counts (D) at constant intervals, assuming the height of the peak of an i-th polymer species above the base line to be Hi and calculating it on the basis of the following equation (A):

$$(Mn)av \text{ (number average molecular weight)} = \Sigma iM_iN_i/\Sigma iN_i = \Sigma iH_iD/\Sigma i(H_iD/M_i) = \Sigma iH_i/\Sigma i(H_i/M_i)$$

Thus the following relation can be obtained:

$$(Mn)av = 1/[\Sigma i(1/M_i)(H_i/\Sigma jH_j)] \quad (A)$$

In the above equations, Ni represents the number of i-th polymer species and Mi represents the molecular weight of the i-th polymer species. In this respect, Mi can be obtained from the foregoing calibration curve.

The peptide-containing polyethylene glycol derivative of the present invention has, a core sequence of a cell-cohesive protein (RGD or EILDVPST) (SEQ ID NO:1) and is adhered to cells through the core sequence according to a mechnism similar to that for the cell-cohesive protein. Therefore, it serves as agonists or antagonists of the cell-cohesive protein and exhibits a wide variety of biological activities such as immunoregulating activity, wound-healing activity, activity for inhibiting platelet coagulation in blood vessels due to cancer cells and nervous disorder-healing activity.

Thus, at least one of the peptide-containing polyethylene glycol derivatives of the present invention can be administered to patients optionally together with conventional carriers or pharmaceutical auxiliary agents as wound-healing agents, immunoregulating agents or platelet coagulation/cohesion-inhibiting agents. In particular, the derivatives are preferably used as animal cell cohesion-inhibiting agents or platelet coagulation/cohesion-inhibiting agents. The administration dose thereof varies depending on various factors such as conditions of disease to be treated, age and weight of patients, but generally ranges from 0.2 μg/kg to 400 mg/kg a day.

The peptide-containing polyethylene glycol derivative may be administered through various routes which are generally used for the administration of peptide-containing medicines. For instance, it is preferebly administered parenterally, e.g., intravenously, intramuscularly and subcutaneously. In the preparation of injectable pharmaceutical preparations containing the peptide-containing polyethylene glycol derivatives, the derivative is dissolved in, for instance, phosphate-buffered saline (PBS: NaH$_2$PO$_4$, 0.005 M; NaCl, 0.07 M) or physiological saline to give an injectable solution as described hereinbelow, or dissolved in, for instance, about 0.1 N aqueous acetic acid solution and then lyophilized to give a lyophilized preparation. These pharmaceutical preparations may comprise a conventional stabilizer such as glycine and albumin. In addition, collagen and liposome may be used as carriers for extending the half-life of the derivatives in the blood.

Further, the peptide-containing polyethylene glycol derivative may be orally administered in the form of microcapsule by encapsulating the derivative in liposomes. Moreover, if it is formulated in the form of, for instance, suppository, sublingual tablets and nasal sprays, it can be absorbed through mucous other than digestive tracts.

The present invention will hereinafter be explained in more detail with reference to the following working Examples, but the present invention is by no means limited to these specific Examples.

EXAMPLE 1

Preparation Example of Compound A-(1) of the present invention will be given below.

Compound A-(1) was prepared according to the following reaction scheme. In this respect, amino acids, various protective groups and agents for eliminating the protective groups are expressed in terms of abbeviations currently used. Compounds other than Compound A-(1) can also be prepared in the manner herein exemplified.

Bzl: benzyl group
TFA: trifluoroacetic acid
Boc: t-butoxycarbonyl group
HOBt: 1-hydroxybenzotriazole
Z: benzyloxycarbonyl group
DCC: dicyclohexylcarbodiimide

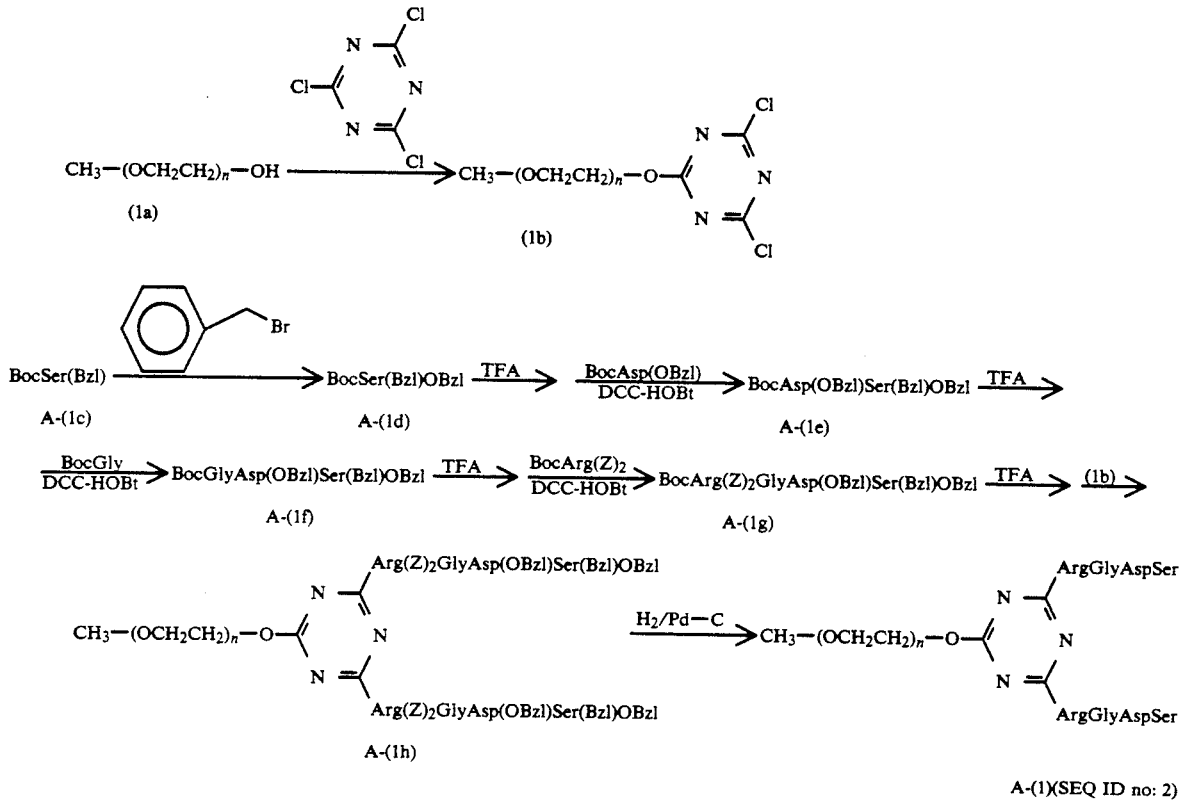

A-(1)(SEQ ID no: 2)

The preparation of Compound A-(1) will be detailed below in accordance with the reaction scheme.

Synthesis of Compound (1b)

Polyethylene glycol monomethyl ether (1a) having an average molecular weight of 5000 and purchased from Ardrich Company (10 g, 2 mmole) was sufficiently dried according to the method described in Biochem. Biophys. Res. Commun., 83, 1978, p. 385; and Life Sciences, 33, 1983, p. 1467, added with 100 ml of toluene, 5 g of sodium carbonate and 1.1 g (6 mmole) of cyanuric chloride and stirred at 80° C. for 120 hours. After allowing the reaction solution to cool down to room temperature, the solution was filtered and the filtrate is added with hexane to to be crystallized. Further the resulting crude crystals were purified by recrystallization from a toluene/acetone/hexane mixed solvent system to give 7 g of white powder.

Preparation of Compound A-(1d)

A mixture of Compound A-(1c) (29.5 g, 0.1 mole) purchased from Kokusan Chemical Co.,Ltd., triethylamine (14 ml), benzyl bromide (17.1 g) and ethyl acetate (200 ml) was refluxed under heating for 3 hours in accordance with the method disclosed in Chem. Pharm. Bull., 24, 1976, p. 3025. After allowing the reaction solution to cool down to room temperature, the solution was washed with 200 ml each of 1 N aqueous solution of sodium hydrogen carbonate and a saturated aqueous solution of sodium chloride and then dried over anhydrous sodium sulfate. The sodium sulfate was removed by filtration and the resulting filtrate was concentrated under reduced pressure to give a colorless oily product. Then, the reaction product was purified by silica gel chromatography (eluent: hexane/ethyl acetate 40:1 to give 36 g of Compound A-(1d).

Preparation of Compound A-(1e)

Compound A-(1d) (7.71 9, 20 mmole) was dissolved in 20 ml of methylene chloride, added with 20 ml of trifluoroacetic acid and stirred at room temperature for 30 minutes. The solvent was distilled off under reduced pressure, 100 ml of chloroform was added to the residue, the solution was washed several times with 100 ml each of 1 N aqueous solution of sodium hydrogen carbonate and a saturated sodium chloride aqueous solution and then dried over anhydrous sodium sulfate. The sodium sulfate was removed by filtration and the filtrate was concentrated under reduced pressure to give a colorless oily product. A mixture of the oily product, BocAsp(OBzl) (6.47 g, 20 mmole; purchased from Kokusan Chemical Co.,Ltd.), DCC (4.54 g, 22 mmole), HOBt (2.76 g, 18 mmole) and DMF (80 ml) was stirred at 0° C. for 3 hours and then at room temperature for 12 hours. The resulting DCUrea was removed, then the solvent was distilled off under reduced pressure. The residue was added with 100 ml of chloroform, washed with 200 ml each of 1 N aqueous solution of sodium hydrogen carbonate and a saturated aqueous solution of sodium chloride and dried over anhydrous sodium sulfate. The sodium sulfate was removed by filtration and the filtrate was concentrated under reduced pressure to give a concentrate which showed a single spot in thin layer chromatography (TLC) and, therefore, was used in the subsequent reaction without further purification.

Preparation of Compound A-(1f)

The same procedures as used in the preparation of Compound A-(1e) were repeated. The protective groups of Compound A-(1e) were removed with TFA and then BocGly (3.50 g, 20 mmole; purchased from Kokusan Chemical Co.,Ltd.), DCC (4.54 g, 22 mmole), HOBt (2.76 g, 18 mmole) and DMF (80 ml) were added to the product to perform a condensation reaction. The resulting product showed a single spot in TLC and, therefore, was used in the subsequent reaction without further purification.

Preparation of Compound A-(1g)

The same procedures as used in the preparation of Compound A-(1e) were repeated. The protective groups of Compound A-(1f) were removed with TFA and then BocArg(Z), (10.83 g, 20 mmole; purchased from Kokusan Chemical Co.,Ltd.), DCC (4.54 g, 22 mmole), HOBt (2.76 g, 18 mmole) and DMF (80 ml) were added to the product to perform a condensation reaction. The reaction product was purified by silica gel chromatography (eluent: chloroform/methanol 99:1) to give 14.4 g of Compound A-(1g) as white powder.

Preparation of Compound A-(1h)

Compound A-(1g) (1.03 g, 1 mmole) was dissolved in 10 ml of methylene chloride, added with 10 ml of TFA and stirred at room temperature for 30 minutes. After distilling off the solvent under reduced pressure, the resultant residue was added with 100 ml of chloroform, washed several times with 100 ml each of 1 N sodium hydrogen carbonate and a saturated aqueous solution of sodium chloride and then dried over anhydrous sodium sulfate. The sodium sulfate was removed by filtration and the filtrate was concentrated under reduced pressure to give white powder. A mixture of the resulting powder, Compound (Ib) (2.5g), triethylamine (0.1 g) and chloroform (50 ml) was stirred at room temperature for 24 hours. The resulting product was purified by gel filtration (Sephadex LH-60) to give 3.1 g of Compound A-(1h).

Preparation of Compound A-(1)

Compound A-(1h) (3.1 g) was dissolved in 50 ml of acetic acid and added with 1 g of 10% palladium on carbon and hydrogenolysis was carried out at room temperature and atmospheric pressure for 24 hours. The catalyst was removed by filtration through Cerite and the resulting filtrate was distilled off under reduced pressure. The resulting product was purified by gel filtration (Sephadex LH-60) to give 2.5 g of Compound A-(1).

Amino Acid Analysis: Gly (1.03); Asp (0.98); Ser (0.92)

Number Average Molecular Weight: 6000

Example 2

Compound A-(2) was prepared in the same manner as used in Example 1 except that a polyethylene glycol derivative of the formula [V] was prepared by utilizing polyethylene glycol monomethyl ether having an average molecular weight of 5,000. Analytical values of Compound A-(2) are summarized in Table 1.

Example 3

Compound A-(3) was prepared in the same manner as used in Example 1 except that a polyethylene glycol derivative [IV] was prepared by utilizing polyethylene glycol monomethyl ether having an average molecular weight of 2,000 and that the protected peptide was sequencially extended at the N-teminal side by using BocAsp(OBzl)OBzl as a starting material. Analytical values of Compound A-(3) are summarized in Table 1.

Example 4

Compound A-(4) was prepared in the same manner as used in Example 1 except that a polyethylene glycol derivative [v] was prepared by utilizing polyethylene glycol monomethyl ether having an average molecular weight of 750. Analytical values of Compound A-(4) are summarized in Table 1.

Example 5

Compound A-(5) was prepared in the same manner as used in Example 1 except that a polyethylene glycol derivative [IV] was prepared by utilizing polyethylene glycol monomethyl ether having an average molecular weight of 5,000 and that the protected peptide was sequencially extended at the N-teminal side using Boc-ProOBzl as a starting material. Analytical values of Compound A-(5) are summarized in Table 1.

Example 6

Compound A-(6) was prepared in the same manner as used in Example 1 except that a polyethylene glycol derivative [Iv] was prepared by utilizing polyethylene glycol monomethyl ether having an average molecular weight of 5,000 and that the protected peptide was sequencially extended at the N-teminal side using Boc-ProNH$_2$ as a starting material. Analytical values of Compound A-(6) are summarized in Table 1.

TABLE 1

| Compound | $(Mn)_{av}$ | Amino Acid Analysis |
|---|---|---|
| A-(2) | 11,000 | Gly (1.05), Asp (0.97), Ser (0.92) |
| A-(3) | 2,000 | Gly (2.02), Asp (1.98), Arg (1.01) |
| A-(4) | 1,500 | Arg (1.03), Gly (0.99), Asp (1.00) |
| A-(5) | 6,000 | Gly (1.10), Asp (0.95), Ser (0.88) Pro (0.94) |
| A-(6) | 6,500 | Arg (1.09), Gly (0.99), Asp (0.96) Ser (0.87), Pro (0.92) |

Example 7

Compound B-(1) was prepared in accordance with the following reaction scheme:

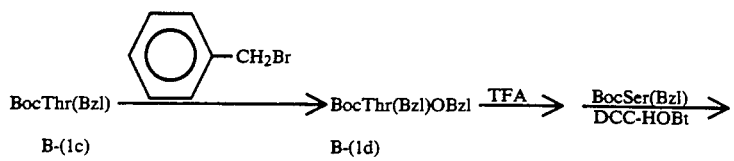

-continued

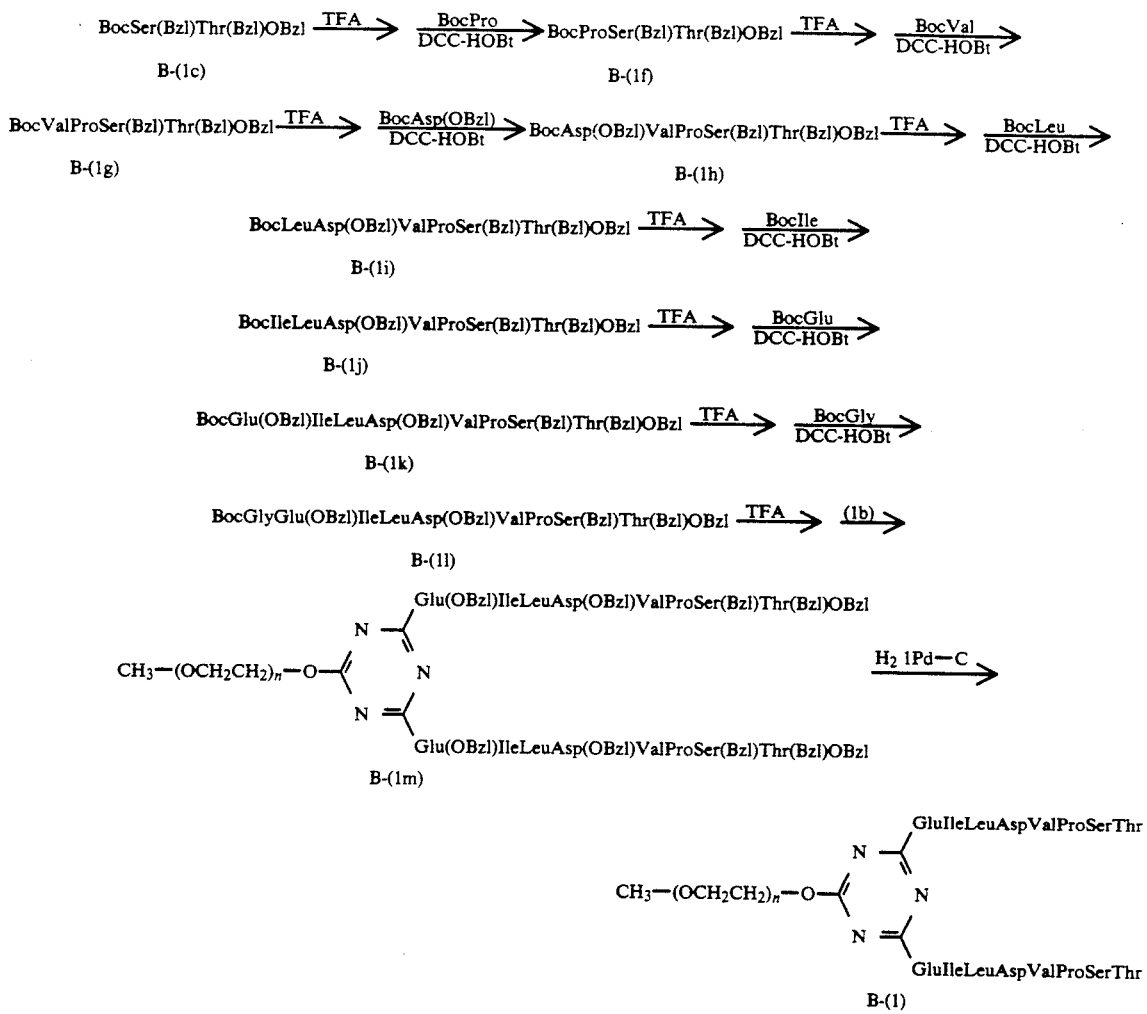

Preparation of Compound B-(1d)

A mixture of Compound B-(1c) (30.9 g, 0.1 mole; purchased from Kokusan Chemical Co.,Ltd.), triethylamine (14 ml), benzyl bromide (17.1 g) and ethyl acetate (200 ml) was refluxed under heating for 3 hours. After allowing the reaction solution to cool down to room temperature, it was washed with 200 ml each of a 1N aqueous sodium hydrogen carbonate and a saturated aqueous solution of sodium chloride and dried over anhydrous sodium sulfate. The sodium sulfate was removed by filtration and the resulting filtrate was concentrated under reduced pressure to give a colorless oily product. The reaction product was purified by silica gel chromatography (eluent: hexane/ethyl acetate 40:1) to give 39 g of Compound B-(1d).

Preparation of Compound B-(1e)

Compound B-(1d) (7.99 g, 20 mmole) was dissolved in 20 ml Of methylene chloride, added with 20 ml of TFA and stirred at room temperature for 30 minutes. After distilling off the solvent under reduced pressure, the resulting residue was added with 100 ml of chloroform, washed several times with 100 ml each of a saturated aqueous solution of sodium chloride and dried over anhydrous sodium sulfate. The sodium sulfate was removed by filtration and the resulting filtrate was concentrated under reduced pressure to give a colorless oily product. A mixture of the oily product, Boc-Ser(Bzl) (5.90 g, 20 mmole; purchased from Kokusan Chemical Co.,Ltd.), DCC (4.54 g, 22 mmole), HOBt (2.76 g, 18 mmole), N-methylmorpholine (2.2 ml, 20 mmole) and DMF (80 ml) as stirred at 0° C. for 3 hours and then at room temperature for 12 hours. After removing the resulting DCUrea, the solvent was distilled off under reduced pressure. The residue was added with 100 ml of chloroform was added, washed with 200 ml each of a 1 N aqueous sodium hydrogen carbonate solution and a saturated aqueous sodium of sodium chloride and dried over anhydrous sodium sulfate. The sodium sulfate was removed by filtration and the filtrate was concentrated under reduced pressure to give a reaction mixture which was found to show a single spot in TLC (thin layer chromatography) and thus used in the subsequent process without further purification.

Preparation of Compound B-(1f)

Compound B-(1f) was prepared in the same manner as used in the preparation of Compound B-(1e). After deprotection with TFA, Compound B-(1e) was added with BocPro (4.30 g, 20 mmole; available from Kokusan Chemical Co.,Ltd.), DCC (4.54 g, 22 mmole), HOBt (2.76 g, 18 mmole) and DMF (80 ml) to perform condensation reaction. The reaction mixture was found to show only a single spot in TLC and thus used in the subsequent process without further purification.

Preparation of Compound B-(1g)

Compound B-(1g) was prepared in the same manner as used in the preparation of Compound B-(1e). After deprotection with TFA, Compound B-(1f) was added with BocVal (4.35 g, 20 mmole; available from Kokusan Chemical Co.,Ltd.), DCC (4.54 g, 22 mmole), HOBt (2.76 g, 18 mmole), N-methylmorpholine (2.2 ml, 20 mmole) and DMF (80 ml) to perform condensation reaction. The resulting reaction mixture was purified by silica gel chromatography (eluent: chloroform/methanol 9:1) to give 13.9 g of Compound B-(1g).

Preparation of Compound B-(1h)

Compound B-(1h) was prepared in the same manner as used in the preparation of Compound B-(1e). After deprofection with TFA, Compound B-(1g) (13.9 g, 18 mmole) was added with BocAsp(OBzl) (5.82 g, 18 mmole), DCC (4.08 g, 19.8 mmole), HOBt (2.48 g, 16.2 mmole), N-methylmorpholine (2.0 ml, 18 mmole) and DMF (80 ml) to perform condensation reaction. The resulting reaction mixture was purified by silica gel chromatography (eluent: chloroform/methanol 9:1) to give 16.7 g of Compound B-(1h).

Preparation of Compound B-(1i)

Compound B-(1i) was prepared in the same manner as used in the preparation of Compound B-(1e). After deprotection with TFA, Compound B-(1h) (14.7 9, 15 mmole) was added with BocLeu (3.47 g, 15 mmole), DCC (3.40 g, 16.5 mmole), HOBt (2.07 g, 13.5 mmole), N-methylmorpholine (1.7 ml, 15 mmole) and DMF (70 ml) to perform condensation reaction. The resulting reaction mixture was purified by silica gel chromatography (eluent: chloroform/methanol 9:1) to give 15.6 g of Compound B-(1i).

Preparation of Compound B-(1j)

Compound B-(1j) was prepared in the same manner as used in the preparation of Compound B-(1e). After deprotection with TFA, Compound B-(1i) (10.9 g, 10 mmole) was added with BocIle (2.31 g, 10 mmole), DCC (2.27 g, 11 mmole), HOBt (1.38 g, 9 mmole), N-methylmorpholine (1.1 ml, 10 mmole) and DMF (50 ml) to perform condensation reaction. The resulting reaction mixture was purified by silica gel chromatography (eluent: c hloroform/methanol 9:1) to give 11.4 g of Compound B-(1j).

Preparation of Compound B-(1k)

Compound B-(1k) was prepared in the same manner as used in the preparation of Compound B-(1e). After deprotection with TFA, Compound B-(1j) (6.0 g, 5 mmole) was added with BocGlu(OBzl) (1.69 g, 5 mmole), DCC (1.13 g, 5.5 mmole), HOBt (0.69 g, 4.5 mmole), N-methylmorpholine (0.55 ml, 5 mmole) and DMF (30 ml) to perform condensation reaction. The resulting reaction mixture was purified by silica gel chromatography (eluent: chloroform/methanol 9:1) to give 6.4 g of Compound B-(1k).

Preparation of Compound B-(1l )

Compound B-(1l) was prepared in the same manner as used in the preparation of Compound B-(1e). After deprotection with TFA, Compound B-(1k) (3.56 g, 2.5 mmole) were added with BocGly (0.44 g, 2.5 mmole), DCC (0.57 g, 2.75 mmole), HOBt (0.34 g, 2.25 mmole), N-methylmorpholine (0.27 ml, 2.5 mmole) and DMF (20 ml) to perform condensation reaction. The resulting reaction mixture was purified by silica gel chromatography (eluent: chloroform/methanol 9:1) to give 3.63 g of Compound B-(1l).

Preparation of Compound B-(1m)

Compound B-(1e) (1.48 g, 1 mmole) was dissolved in 10 ml of methylene chloride, added with 10 ml of TFA and stirred at room temperature for 30 minutes. After distillation of the solvent under reduced pressure, the residue was added with 100 ml of chloroform washed several times with 100 ml each of a 1N aqueous solution of sodium hydrogen carbonate and a saturated aqueous solution of sodium chloride and dried over anhydrous sodium sulfate. The sodium sulfate was removed by filtration and the filtrate was concentrated under reduced pressure to give white powder. A mixture of the white powder, Compound (Ib) (2.5 g) prepared in the same manner as used in Example 1, triethylamine (0.1 g) and chloroform (50 ml) was stirred at room temperature for 24 hours. The reaction mixture was purified by gel filtration (Sephadex LH-60) to give 3.5 g of Compound B-(1m).

Preparation of Compound B-(1)

Compound B-(1m) (3.5 g) was dissolved in 50 ml of acetic acid and 1 g of 10% palladium on carbon was added to the solution to perform hydrogenolysis at room temperature and atmospheric pressure for 24 hours. The catalyst was removed by filtration through Cerite and the solvent was distilled off under reduced pressure. The resulting reaction mixture was Purified by gel filtration (Sephadex LH-60) to give 2.9 g of Compound B-(1).

Amino Acid Analysis: Glu (1.00), Ile (0.98), Leu (1.02), Asp (1.01), Val (1.04), Pro (0.97), Ser (0.82), Thr (0.85)

Number Average Molecular Weight: 7,000

Examples 8 to 10

In the same manner as used in Example 7, Compounds B-(2), B-(3) and B-(4) were prepared. Analytical values of these compounds are summarized in the following Table 2.

TABLE 2

| Compound | $(Mn)_{av}$ | Amino Acid Analysis |
|---|---|---|
| B-(2) | 12,000 | Glu (0.97), Ile (1.01), Leu (0.99), Asp (0.98), Val (1.03), Pro (0.96), Ser (0.85), Thr (0.82) |
| B-(3) | 9,000 | Glu (0.47), Ile (1.04), Leu (1.00), Asp (1.01), Val (1.05), Pro (0.89), Ser (0.79), Thr (0.80) |
| B-(4) | 3,500 | Glu (0.99), Ile (0.97), Leu (1.03), Asp (1.00), Val (0.98), Pro (0.95), Ser (0.82), Thr (0.81) |

Preparation of Medicines

The peptide-containing polyethylene glycol derivative of the invention A-(1), was dissolved in physiological saline at a concentration of 100 µg/ml to give a preparation for injection. This pharmaceutical preparation could be used as an agent for inhibiting adhesion of animal cells and an agent for inhibiting coagulation/cohesion of blood platelets.

Test Example

A. Determination of Cell Adhesion-Inhibitory Activity

The peptide-containing polyethylene glycol derivatives of the present invention can inhibit adhesion of cells to fibronectin and vitronectin. A method for determining the activity thereof will be described below. The competitive assay used herein has widely been used in the field of biochemistry and are detailed in, for instance, "Method in Enzymology", 82, 1981, pp. 803; and J. P. KOKAI Nos. Hei 1-309682 and Hei 2-174797.

Experimental Methods

1. Preparation of Adsorption Plate

Commercially available fibronectin (derived from human; purchased from Seikagaku Kogyo Co.,Ltd.) and vitronectin (derived from human; purchased from Funakoshi Co.,Ltd.) each was diluted to 1.0 μl/ml and 2.0 μl/ml with PBS ($NaH_2PO_4$ 0.005 M + NaCl 0.07M), 0.5 ml of the resulting diluted solution was dispensed into a plastic plate having 24 wells and incubated at 37° C. overnight to coat the plate. Then bovine serum albumin (BSA 1%) was added followed by incubation at 37° C. for one hour to inhibit the occurrence of nonspecific adsorption, then washing with PBS in the usual manner and sufficient drainage to give an adsorption plate.

2. Adhesion-Inhibitory Test

A solution of the peptide-containing polyethylene glycol derivative diluted with Dulbeccos Modified Eagles Medium (hereinafter referred to as "DMEM") was dispensed into the wells of the plate prepared above in an amount of 0.25 to 1.5 ml, 0.25 ml of a suspension of endothelium cells of blood vessel ($4 \times 10^6$ cells/ml) was dispensed into the wells and incubated at 37° C. for one hour to thus cause cohesion of the cells. The plate was washed three times with DMEM medium to remove non-cohesive cells, then the cohered cells were peeled off with 0.025% EDTA trypsin solution and stained with a 2% Trypan Blue solution to determine the number of the cohered cells. The results thus obtained are summarized in the following Table 3 and 4. In these Tables, RGD represents an arginine-glycine-aspartic acid tripeptide, GRGDS a glycine-arginine-glycine-aspartic acid-serine pentapeptide (SEQ ID NO:9), EILDVPST a glutamic acid-isoleucineleucine-aspartic acid-valine-proline-serine-threonine octapeptide (SEQ ID NO:1) and PEG-deriv. a peptide-containing polyethylene glycol derivative.

TABLE 3

| 1) Cell Adhesion-Inhibitory Effect Against Fibronectin ($\times 10^2$ cells/well) | | | | | |
|---|---|---|---|---|---|
| PEG-deriv. | Concentration (mg/ml) | | | | |
| Used | 0 | 0.25 | 0.5 | 1.0 | 1.5 |
| RGD | 157 | 154 | 160 | 142 | 83 |
| GRGDS (SEQ ID No: 9) | 157 | 152 | 148 | 91 | 84 |
| Compound A-(1) | 157 | 59 | 28 | 26 | 19 |
| Compound A-(2) | 157 | 73 | 49 | 33 | 28 |
| Compound A-(3) | 157 | 51 | 43 | 27 | 15 |
| Compound A-(4) | 157 | 43 | 39 | 18 | 16 |
| Compound A-(5) | 157 | 40 | 32 | 19 | 10 |
| Compound A-(6) | 157 | 39 | 30 | 17 | 9 |

| 2) Cell Adhesion-Inhibitory Effect Against Vitronectin ($\times 10^2$ cells/well) | | | | | |
|---|---|---|---|---|---|
| PEG-deriv. | Concentration (mg/ml) | | | | |

TABLE 3-continued

| Used | 0 | 10 | 50 | 100 | 300 | 500 |
|---|---|---|---|---|---|---|
| RGD | 243 | 154 | 136 | 107 | 79 | 63 |
| GRGDS (SEQ ID No: 9) | 243 | 156 | 119 | 81 | 64 | 62 |
| Compound A-(1) | 243 | 57 | 44 | 40 | 37 | 40 |
| Compound A-(2) | 243 | 66 | 58 | 47 | 34 | 30 |
| Compound A-(3) | 243 | 74 | 62 | 54 | 45 | 32 |
| Compound A-(4) | 243 | 73 | 57 | 56 | 46 | 34 |
| Compound A-(5) | 243 | 49 | 41 | 35 | 30 | 28 |
| Compound A-(6) | 243 | 47 | 40 | 36 | 29 | 27 |

TABLE 4

| Rate of Cell-Adhesion Against Fibronectin (%)* | | | | | |
|---|---|---|---|---|---|
| PEG-deriv. | Concentration (mg/ml) | | | | |
| Used | 0 | 0.25 | 0.5 | 1.0 | 2.0 |
| EILDVPST (SEQ ID No: 1) | 100 | 69 | 25 | 22 | 18 |
| Compound B-(1) | 100 | 53 | 20 | 17 | 14 |
| Compound B-(2) | 100 | 56 | 24 | 20 | 17 |
| Compound B-(3) | 100 | 55 | 20 | 18 | 15 |
| Compound B-(4) | 100 | 57 | 23 | 18 | 16 |

*Percentage of adhered cell numbers on the basis of the same obtained at the concentration of 0

B. Determination of Platelet Coagulation-Inhibitory Activity

The platelet coagulation-inhibitory activity of the peptide-containing polyethylene glycol derivative of the present invention was assayed, in vitro, using human plasma rich in platelet. The experimental method will be described below.

To fresh human blood, there was added 1/9 volume of a 3.8% sodium citrate solution, the resulting mixture was centrifuged (1000 rpm, 10 minutes) and the upper layer was separated as a plasma rich in platelet. To 200 μl of the plasma, there was added 25 μl of a solution of the peptide-containing polyethylene glycol derivative (max 1.5 mg/ml), the resulting mixture was incubated at 37° C. for 3 minutes, and then 25 μl of a 20 to 50 μM ADP (adenisine diphosphate) solution or a 200 μg/ml collagen solution was added to evaluate the extent of coagulation in terms of transmittance determined by an aggregometer. The results thus obtained are summarized in the following Tables 5 and 6.

Rate of Coagulation Inhibition = $(1 - T/T_0) \times 100\%$ $T_0$: Transmittance observed when the peptide-containing polyethylene glycol derivative was not added.
T: Transmittance observed when the peptide-containing polyethylene glycol derivative was added.
$IC_{50}$: Concentration of the compound to obtain 50% coagulation inhibition.

TABLE 5

| Platelet Coagulation-Inhibitory Activity $IC_{50}$ (μg/ml) | | |
|---|---|---|
| Compound | ADP Stimulation | Collagen Stimulation |
| A-(1) | 20 | 20 |
| A-(2) | 23 | 22 |
| A-(3) | 18 | 19 |
| A-(4) | 27 | 25 |
| A-(5) | 20 | 18 |
| A-(6) | 17 | 15 |
| RGD | 26 | 21 |
| GRGDS | 34 | 23 |

TABLE 6

| Platelet Coagulation-Inhibitory Activity IC$_{50}$ (μg/ml) | | |
| --- | --- | --- |
| Compound | ADP Stimulation | Collagen Stimulation |
| B-(1) | 19 | 19 |
| B-(2) | 22 | 23 |
| B-(3) | 17 | 18 |
| B-(4) | 26 | 23 |
| EILDVPST | 27 | 25 | onine residues respectively; [X] and [Y] each represents an amino acid or peptide residue which may be present or absent; n is an integer ranging from 1 to 150; m is an integer ranging from 1 to 5 and Z represents -OH or -NH$_2$, provided that the peptide residue [IIIb] SEQ ID NO:1), as ([X]-[SEQ ID NO:1)-[Y])$_m$ and the triazine ring is bonded at the position of [X] (if [X] is absent, at the position of Glu) or [Y] (or if [Y] is absent, at the position of Thr), or a salt thereof.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

```
Glu Ile Leu Asp Val Pro Ser Thr
1               5
```

What is claimed is:

1. A peptide-containing polyethylene glycol derivative represented by the following formula [I] or [II]:

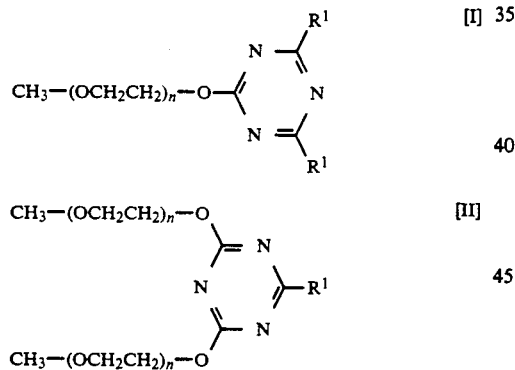

wherein each R$^1$ independently represents a peptide residue represented by the following formula [IIIa] or (IIIb):

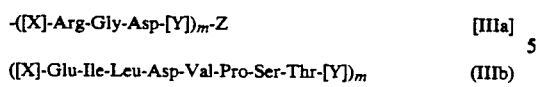

-([X]-Arg-Gly-Asp-[Y])$_m$-Z    [IIIa]

([X]-Glu-Ile-Leu-Asp-Val-Pro-Ser-Thr-[Y])$_m$    (IIIb)

wherein Arg, Gly, Asp, Glu, Ile, Leu, Val, Pro, Ser and Thr represent arginine, glycine, aspartic acid, glutamic acid, isoleucine, leucine, valine, proline, serine and thre- 2. A compound of claim 1 wherein , [X] and [Y] in the formulae [IIIa] and (IIIb) are present and each independently represents an amino acid residue selected from the group consisting of serine, glycine, valine, asparagine, proline, cysteine and threonine residues or a peptide residues constituted by the foregoing amino acid residues.

3. The compound of claim 2 wherein R$^1$ represents a peptide residue represented by the formula [IIIa] and [X] and [Y] each represents a peptide residue comprising 2 to 3 amino acid residues.

4. The compound of claim 2 wherein R$^1$ represents a peptide residue represented by the formula [IIIa] and [X] represents a glycine residue.

5. The compound of claim 2 wherein [Y] represents a serine residue.

6. The compound of claim 3 wherein [Y] represents a serine-proline peptide residue.

7. The compound of claim 1 wherein both [X] and [Y] are absent.

8. The compound of claim 1 wherein n is an integer ranging from 5 to 120.

9. The compound of claim 1 wherein m is an integer ranging from 1 to 3.

10. The compound of claim 1 wherein it is a sodium, potassium, ammonium or magnesium salt or hydrochloride, sulfate, nitrate or acetate.

11. The compound of claim 1 which is any one of the following compounds A-(1) to A-(6) and B-(1) to B-(4):

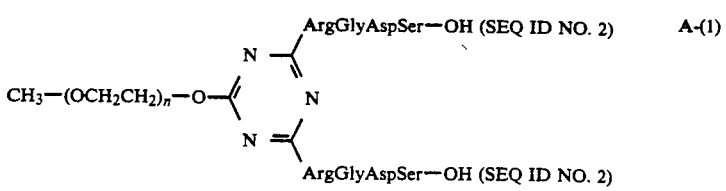

-continued
Number average molecular weight: 6,000
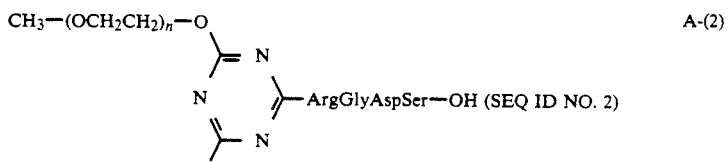
A-(2)
Number average molecular weight: 11,000
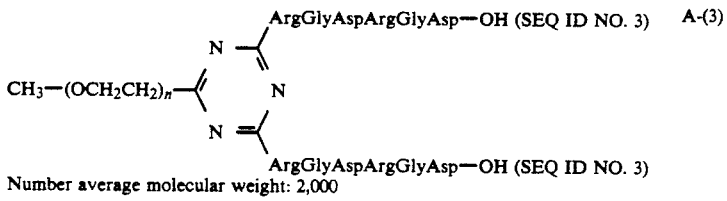
A-(3)
Number average molecular weight: 2,000
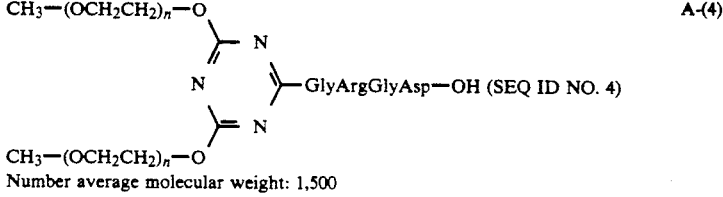
A-(4)
Number average molecular weight: 1,500
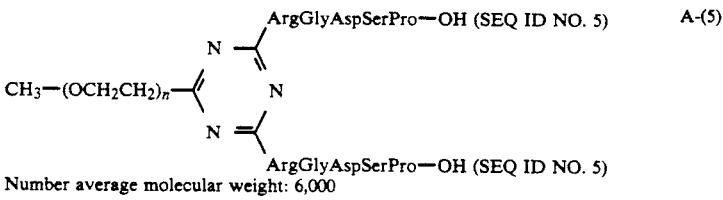
A-(5)
Number average molecular weight: 6,000
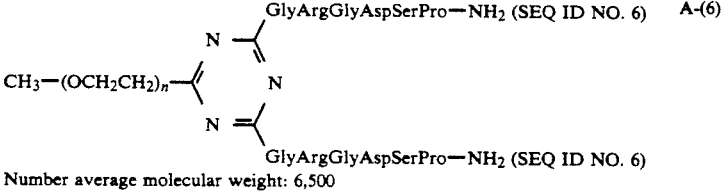
A-(6)
Number average molecular weight: 6,500
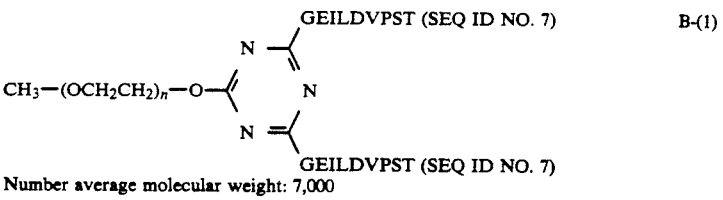
B-(1)
Number average molecular weight: 7,000
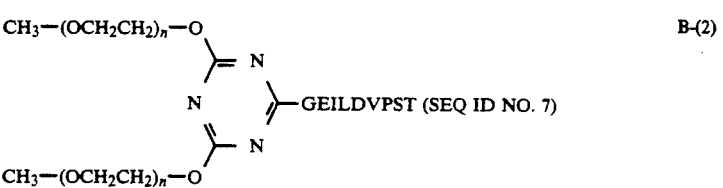
B-(2)
Number average molecular weight: 12,000
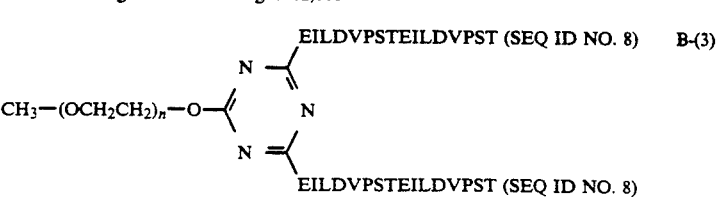
B-(3)
Number average molecular weight: 9,000

-continued

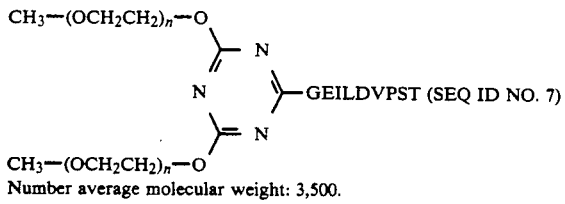

Number average molecular weight: 3,500.

12. A pharmaceutical composition for inhibiting adhesion of animal cells comprising:

(i) an effective amount of a peptide-containing polyethylene glycol derivative, or a pharmaceutically acceptable salt thereof, represented by the following formulas (I) or (II):

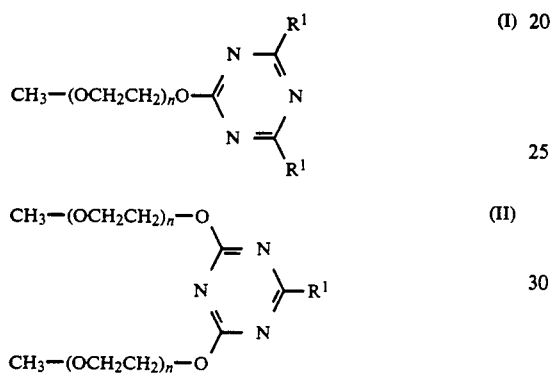

wherein each $R^1$ independently represent a peptide residue represented by the following formula (IIIa) or (IIIb):

-((X)-Arg-Gly-Asp-(Y)))$_m$-Z   (IIIa)

((X)-Glu-Ile-Leuasp-Val-Pro-Ser-Thr-(Y))$_m$   (IIIb) (SEQ ID NO:1)

wherein Arg, Gly, Asp, Glu, Ile, Leu, Val, Pro, Ser and Thr represent arginine, glycine, aspartic acid, glutamic acid, isoleucine, leucine, valine, proline, serine and threonine residues respectively: (X) and (Y) each represent an amino acid or peptide residue which may be present or absent; n is an integer ranging from 1 to 150; m is an integer ranging from 1 to 5 Z represents —OH— or —NH$_2$, provided that the peptide residue (IIIb) and the triazine ring is bonded at the position of (X) (if (X) is absent, at the position of Glu) or (Y) (or if (Y) is absent, at the position of Thr), and (ii) a pharmaceutically acceptable carrier.

13. A pharmaceutical composition for inhibiting coagulation/cohesion of blood platelets comprising:

(i) an effective amount of peptide-containing polyethylene glycol derivative, or a pharmaceutically acceptable salt thereof, represented by the following formula (I) or (II):

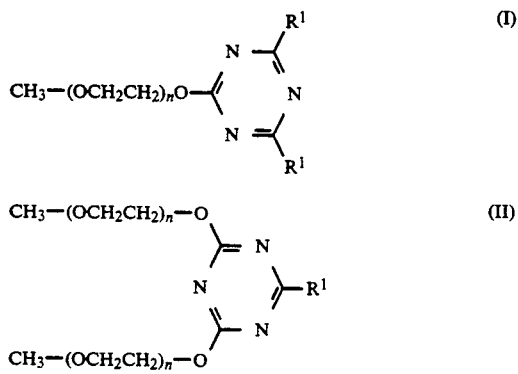

wherein each $R^1$ independently represents a peptide residue represented by the following formula (IIIa) or (IIIb):

-((X)-Arg-Gly-Asp-(Y)))$_m$-Z   (IIIa)

((X)-Glu-Ile-Leu-Asp-Val-Pro-Ser-Thr-(Y))$_m$   (IIIb) (SEQ ID NO:1)

wherein Arg, Gly, Asp, Glu, Ile, Leu, Val, Pro, Ser and Thr represent arginine, glycine, aspartic acid, glutamic acid, isoleucine, leucine, valine, proline, serine and threonine residues respectively: (X) and (Y) each represent an amino acid or peptide residue which may be present or absent; n is an integer ranging from 1 to 150; m is an integer ranging from 1 to 5 Z represents —OH— or —NH$_2$, provided that the peptide residue (IIIb) and the triazine ring is bonded at the position of (X) (if (X) is absent, at the position of Glu) or (Y) (or if (Y) is absent, at the position of Thr), and (ii) a pharmaceutically acceptable carrier.

* * * * *

UNITED STATES PATENT AND TRADEMARK OFFICE
CERTIFICATE OF CORRECTION

PATENT NO. : 5,229,366
DATED : July 20, 1993
INVENTOR(S) : Tsukada et al

It is certified that error appears in the above-indentified patent and that said Letters Patent is hereby corrected as shown below:

Column 19,

Delete the present Sequence Listing Section

"(1) GENERAL INFORMATION:

(iii) NUMBER OF SEQUENCES: 1

(2) INFORMATION FOR SEQ. ID. NO.: 1

(i) SEQUENCE CHARACTERISTICS:
    (A) LENGTH: 8 amino acids
    (B) TYPE: amino acid
    (C) STRANDEDNESS: single
    (D) TOPOLOGY: linear"

(ii) MOLECULE TYPE: peptide (xi) SEQUENCE DESCRIPTION: SEQ ID NO:1:

Glu Ile Leu Asp Val Pro Ser Thr "
1               5

UNITED STATES PATENT AND TRADEMARK OFFICE
CERTIFICATE OF CORRECTION

PATENT NO. : 5,229,366
DATED : July 20, 1993
INVENTOR(S) : Tsukada et al

It is certified that error appears in the above-indentified patent and that said Letters Patent is hereby corrected as shown below:

and insert the following:

--(1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Glu Ile Leu Asp Val Pro Ser Thr
   1               5

(2) INFORMATION FOR SEQ ID NO:2:

(i) SEQUENCE CHARACTERISTICS:
      (A) LENGTH: 4 amino acids
      (B) TYPE: amino acid
      (C) STRANDEDNESS: single
      (D) TOPOLOGY: linear (ii) MOLECULE TYPE: peptide

UNITED STATES PATENT AND TRADEMARK OFFICE
CERTIFICATE OF CORRECTION

PATENT NO. : 5,229,366
DATED : July 20, 1993
INVENTOR(S) : Tsukada et al

It is certified that error appears in the above-indentified patent and that said Letters Patent is hereby corrected as shown below:

(xi) SEQUENCE DESCRIPTION: SEQ ID NO:2:

Arg Gly Asp Ser
    1

(2) INFORMATION FOR SEQ ID NO:3:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Arg Gly Asp Arg Gly Asp
    1               5

(2) INFORMATION FOR SEQ ID NO:4:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide

UNITED STATES PATENT AND TRADEMARK OFFICE
CERTIFICATE OF CORRECTION

PATENT NO. : 5,229,366
DATED : July 20, 1993
INVENTOR(S) : Tsukada et al

It is certified that error appears in the above-indentified patent and that said Letters Patent is hereby corrected as shown below:

(xi) SEQUENCE DESCRIPTION: SEQ ID NO:4:

Gly Arg Gly Asp
    1

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Arg Gly Asp Ser Pro
    1              5

(2) INFORMATION FOR SEQ ID NO:6:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide

UNITED STATES PATENT AND TRADEMARK OFFICE
CERTIFICATE OF CORRECTION

PATENT NO. : 5,229,366
DATED : July 20, 1993
INVENTOR(S) : Tsukada et al

It is certified that error appears in the above-indentified patent and that said Letters Patent is hereby corrected as shown below:

```
     (xi) SEQUENCE DESCRIPTION: SEQ ID NO:6:

Gly Arg Gly Asp Ser Pro
         1                   5

(2) INFORMATION FOR SEQ ID NO:7:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:7:

Gly Glu Ile Leu Asp Val Pro Ser Thr
         1                   5

(2) INFORMATION FOR SEQ ID NO:8:

(i) SEQUENCE CHARACTERISTICS:
          (A) LENGTH: 16 amino acids
          (B) TYPE: amino acid
          (C) STRANDEDNESS: single
          (D) TOPOLOGY: linear (ii) MOLECULE TYPE: peptide
```

UNITED STATES PATENT AND TRADEMARK OFFICE
CERTIFICATE OF CORRECTION

PATENT NO. : 5,229,366
DATED : July 20, 1993
INVENTOR(S) : Tsukada et al

It is certified that error appears in the above-indentified patent and that said Letters Patent is hereby corrected as shown below:

(xi) SEQUENCE DESCRIPTION: SEQ ID NO: 8:

Glu Ile Leu Asp Val Pro Ser Thr Glu Ile Leu Asp Val Pro Ser Thr
1               5               10                  15

(2) INFORMATION FOR SEQ ID NO:9:

(i) SEQUENCE CHARACTERISTICS:
      (A) LENGTH: 5 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:9:

Gly Arg Gly Asp Ser
1               5      --

Signed and Sealed this

Twenty-fifth Day of April, 1995

Attest:

BRUCE LEHMAN

Attesting Officer     Commissioner of Patents and Trademarks